US006689603B2

(12) United States Patent
Pompidou et al.

(10) Patent No.: US 6,689,603 B2
(45) Date of Patent: Feb. 10, 2004

(54) DEVICE FOR IN SITU ANALYSIS AND/OR TREATMENT CONSISTING OF A FLEXIBLE ROD AND MICRO SYSTEM FIXED AT ONE END OF SAID FLEXIBLE ROD

(76) Inventors: Alain Pompidou, 46, quai Henry IV, F-75004 Paris (FR); Albert-Claude Benhamou, 262, rue Saint Jacques, F-75005 Paris (FR)

( * ) Notice: Subject to any disclaimer, the term of this patent is extended or adjusted under 35 U.S.C. 154(b) by 0 days.

(21) Appl. No.: 09/926,351

(22) PCT Filed: Mar. 16, 2001

(86) PCT No.: PCT/FR01/00803

§ 371 (c)(1), (2), (4) Date: Jan. 30, 2002

(87) PCT Pub. No.: WO01/69257

PCT Pub. Date: Sep. 20, 2001

(65) Prior Publication Data

US 2003/0049679 A1 Mar. 13, 2003

Related U.S. Application Data

(60) Provisional application No. 60/246,571, filed on Nov. 8, 2000.

(30) Foreign Application Priority Data

Mar. 17, 2000 (FR) .............................. 00 03474

(51) Int. Cl.⁷ ................................. C12M 1/34
(52) U.S. Cl. ................. 435/287.2; 435/287.3; 435/288.1; 435/288.3
(58) Field of Search ............... 435/287.2, 287.3, 435/288.1, 288.3

(56) References Cited

U.S. PATENT DOCUMENTS

| 5,001,051 | A | | 3/1991 | Miller et al. | |
| 5,081,013 | A | * | 1/1992 | Rovelli et al. | 435/7.92 |
| 5,699,156 | A | * | 12/1997 | Carver | 356/319 |
| 5,804,453 | A | | 9/1998 | Chen | |
| 5,837,196 | A | | 11/1998 | Pinkel et al. | |
| 5,879,897 | A | * | 3/1999 | Koufman | 435/7.4 |
| 5,938,595 | A | | 8/1999 | Glass et al. | |
| 6,235,471 | B1 | * | 5/2001 | Knapp et al. | 435/6 |
| 6,235,473 | B1 | * | 5/2001 | Friedman et al. | 435/6 |

FOREIGN PATENT DOCUMENTS

| JP | 06 027110 | 2/1994 |
| WO | 98 50782 | 11/1998 |
| WO | 00 63437 | 10/2000 |

* cited by examiner

*Primary Examiner*—Kenneth R. Horlick
(74) *Attorney, Agent, or Firm*—Oblon, Spivak, McClelland, Maier & Neustadt, P.C.

(57) ABSTRACT

This invention concerns an apparatus for chemical or biological analysis or treatment in situ comprising (i) a microsystem for investigation of a substrate and/or for delivery of active agents in a substrate and (ii) a flexible rod to one end of which the microsystem is attached and the other end of which is intended for the control of said microsystem. The microsystem is advantageously of the type comprising a support on the surface of which predefined regions are arrayed, each containing different chemical or biological substances for investigation or treatment of the substrate where the microsystem is brought in contact thanks to the flexible rod.

31 Claims, 6 Drawing Sheets

Flexible system for guidance of the support

Fig. 4
.() Anti-M Ab
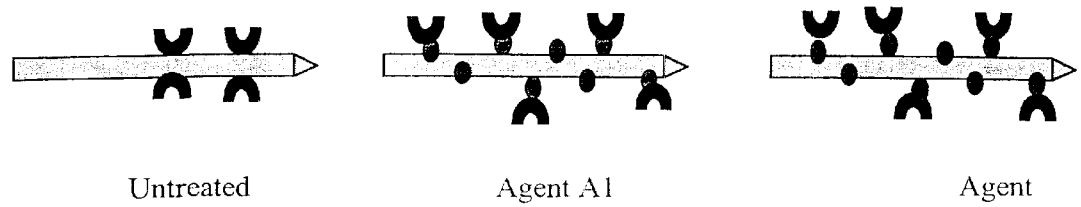
Untreated        Agent A1        Agent
Probes sensitized with the Ab Fig. 5
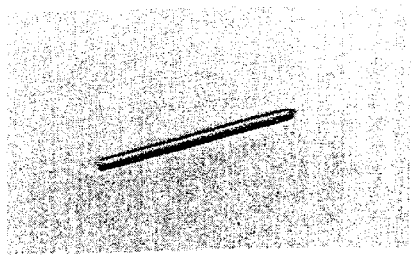
Rigid plastic support
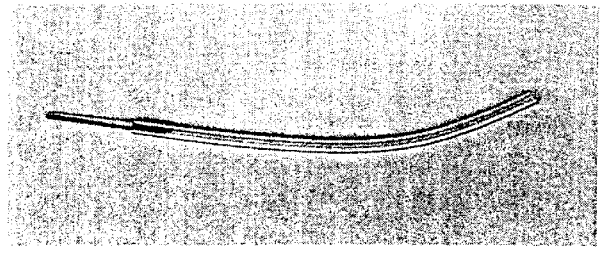
Support inserted in the "guidance" system

DEVICE FOR IN SITU ANALYSIS AND/OR TREATMENT CONSISTING OF A FLEXIBLE ROD AND MICRO SYSTEM FIXED AT ONE END OF SAID FLEXIBLE ROD

This application claims the benefit of the filing date of U.S. application Ser. No. 60/246,571 filed Nov. 8, 2000.

This invention concerns an apparatus making it possible to carry out by remote control an investigation and/or treatment in situ in a substrate, for example, of tissues or organs, consisting of a flexible rod, to one end of which an investigation and/or treatment microsystem is attached.

Investigation microsystems employing an array of biological molecules placed in given positions on a surface are described in the prior art. Those systems, known as "biochips" or DNA chips, are useful for the investigation of polynucleotide or amino acid sequences. Examples of such systems are described, for example, in the European patent applications published under No. 619,321, No. 373,203 and No. 691,978. Other investigation microsystems are, for example, the microanalysis tests using ligand/receptor type reactions or microimmunoanalyses using antigen/antibody type reactions.

Apparatuses for in vivo investigation of organs or tissues are also known in the prior art, such as a catheter consisting of a flexible tube inserted in the vessels or through the natural routes, associated, for example, with a laser, an optical fiber, a probe or a sensor. Those apparatuses can also make possible the administration of active substances like drugs or diagnostic agents, such as, for example, the apparatus described in U.S. Pat. No. 5,938,595.

The inventors have now designed a remote-controlled apparatus for analysis and/or treatment in situ combining the two technologies mentioned above. It appears useful, in fact, to have available new means of investigation and/or treatment in situ in a substrate of an organism in vivo or in vitro the least traumatizing as possible, particularly in the case of a human patient, and which makes it possible to access (i) information useful for diagnosis as well as for screening, for example, for therapeutic indications, or (ii) new methods of administration of active pharmaceutical agents directly in a substrate consisting, for example, of target cells.

This objective is attained according to the present invention thanks to an apparatus for chemical or biological analysis or treatment in situ comprising (i) a microsystem for investigation of a substrate and/or for delivery of active agents in a substrate and (ii) a flexible rod to one end of which the microsystem is attached and the other end of which is intended for the control of said microsystem, and in that, in the case of an investigation, the microsystem is not of the type based on analysis of the emission and detection of a fluorescent signal.

Said microsystem and said flexible rod are advantageously kept together in situ. Thus, according to the invention, said microsystem and said flexible rod remain joined to one another upon use in situ and are separated only before or after the operation in situ, so that the microsystem does not constitute a system implantable or releasable in situ.

In a first embodiment, the microsystem is of the type comprising a support on the surface of which predefined regions are arrayed, each containing different chemical or biological substances for investigation or treatment of the substrate into which the microsystem is brought in contact thanks to the flexible rod. Said surface contains at least two and preferably more than 100 and especially preferably more than 1000 predefined regions on a surface in the order of several $cm^2$ and preferably in the order of 1 $cm^2$ or less. Each predefined area contains a different chemical or biological substance, but the process according to the invention also allows several or even all of said predefined regions to contain the same chemical or biological substance, for example, in case of the same analysis or of delivery of the same active substance in time.

The support can contain several faces, at least one of which consists of an active surface. The latter is the site of one or more biological bonding agents. In the midst of said active surface predefined regions are arrayed.

This surface of approximately one $cm^2$ can be flat and is situated in a single plane, and it can also be ribbon-shaped and spiral-wound on a rigid support which extends the flexible rod and then presents the microsystem of the same nature as the previous one, but of a more elaborate configuration. FIG. 1 represents a working example of an apparatus according to the invention, consisting of a flexible rod (1) like, for example, a deformable catheter, at the end of which the microsystem (2) is inserted in the opening of the flexible rod, the microsystem consisting of a support (3) on which a ribbon (4) is wound or specific antibiodies of an antigen present in the substrate analyzed are fixed. The support (3) is rigid, while the flexible rod (1) is relatively deformable. The flexible rod (1) can be combined with an endovascular exploration system (5) like, for example, an endoscope.

The apparatus of the invention can be combined with an endocavitary to endovascular exploration system making it possible to bring the microsystem in contact with or in proximity to the target substrate.

In a second embodiment, the apparatus of the invention can consist of a flexible rod, possibly combined with an endocavitary or endovascular exploration system. The latter ends in a microsystem consisting of an articulated segment composed of an alternation of rigid substances (platinum ball type) and of more or less hydrophilic gel (hydrogel) on which the reactive groups, molecules or substances are fixed. The active layer surrounding the rigid support can be a flat ribbon or a round cord on which the reagents are deposited and fixed. It can involve ligands and, notably, antigens or antibodies, but also nucleotides. Thus, in this embodiment the microsystem consists of a support coming in the form of a ribbon wound around one end of the flexible rod. An example of this embodiment is represented on FIG. 1 of the attached drawings.

As previously indicated, each predefined area can contain the same active chemical or biological substance, for example, in case of the same analysis or of delivery of the same active substance reproduced in time. Each predefined area can also contain a different chemical or biological substance, and the microsystem then supporting a plurality of different chemical or biological substances is intended to carry out a multiple analysis.

The apparatus according to the invention is useful in:
 the therapeutic field for in situ delivery of agents active in a substrate, and
 the field of diagnosis for in situ analysis of a substrate.

In particular, the apparatus of the invention is useful for therapeutic applications conducted within the framework of guided therapy, as proposed for intracardiac gene therapy aimed at bringing autologous myeloid cells in situ after having evaluated with the endocavitary probe the state of the cell tissue of the myocardial area to be treated. This is with the aid of different systems and, in particular, of the microsystems of diagnosis or therapeutic follow-up of the invention.

Within the scope of the therapeutic applications, the biological and/or chemical substances arrayed in each predefined region of the surface of the microsystem are active agents, notably therapeutic substances. The active agents can be any substance useful in the treatment of diseases requiring an intervention in target cells or tissues, like cancer cells, centers of infection, etc.

Within the scope of the diagnostic applications, the biological and/or chemical substances arrayed in each predefined region of the surface of the microsystem are substances making it possible to detect specific analytes of the substrate where the microsystem is taken, or even radiolabeled substances making possible the remote display of the organ targeted by any known medical imaging technique.

Said substances can be fixed in each predefined region of the support either reversibly, in order possibly to be released again by the microsystem so that they may perform their function "in vivo", after removal of said microsystem, or irreversibly on said surface. Fixation can be carried out by simple adsorption or by means of a coupling product.

The active agents are released in the substrate:
by simple contact with the latter, in which case they are physically protected, as described below, until the microsystem is placed in said substrate, or
thanks to a complementary system of release in the microsystem.

A preferred method of use of the therapeutic application of the apparatus of the invention consists in utilizing active substances which are nucleic acids, like naked DNAs or antisense oligonucleotides, fixed on the surface of the support of the microsystem by hybridization. But the active substances can also be proteins or antibodies fixed on each predefined region thanks to an immunological bond. By way of example of a microsystem forming part of a treatment apparatus according to the invention, one can mention the bionic chips which electrically control cell activity, so as to release therapeutically active agents.

For the applications of diagnosis and, more widely, of analysis of a substrate, the microsystem of the apparatus of the invention is an investigation microsystem.

According to a preferred embodiment of the apparatus of the invention, the chemical or biological substances are capable of reacting with corresponding substances possibly present in the substrate where the investigation microsystem is brought thanks to the flexible rod.

Thus, the microsystem is preferably a receptor/ligand microsystem using pairs of chemical or biological substances in which either or both of the members of the pair are fixed on each predefined region, notably for therapeutic applications.

The microsystem according to the invention advantageously uses biological substances which are polynucleotide or amino acid sequences. The invention envisages as chemical or biological substances present in each predefined region chemical or biological substances constituting:
an array of polynucleotide sequences capable of being hybridized with nucleic acids present in the substrate notably constituting the investigation site, or
an array of peptides, polypeptides or proteins capable of reacting with a corresponding receptor or immunologically with antibodies or antigens present in the substrate notably constituting the investigation site.

But the investigation microsystem can also use chemical substances capable of reacting according to varied chemical reactions with corresponding chemical substances present in the substrate analyzed. Thus, the investigation microsystem according to the invention makes possible the simultaneous analysis of several physiological factors in situ.

Taking into account the diversity of types of biological or chemical reactions capable of being used in the investigation microsystem, the apparatus of the invention makes possible the identification of genes or their components of DNA, of RNA, of pertinent nucleotide sequences or of their specific protein products, but also of agonists and their receptors. It also makes possible in vitro and in vivo the identification of viruses, bacteria, parasites or their specific components, as well as pathogenic agents of prion type.

The apparatus of the invention can thus be used:
for purposes of analysis of different types of genomes and notably for their sequencing,
for identification of cells, tissues and organs or of different types of normal or pathological specific receptors,
for purposes of diagnosis as, for example, thanks to the identification of genes, their component or their product,
for purposes of screening of molecules or chemical or biological substances with known or potential therapeutic characteristics,
for follow-up of the activity of new or already known therapeutic agents (possibility of multistage and repeated guided examinations).

The above list is not exhaustive, and with this information the expert is capable of extending the use of the apparatus of the invention to any other type of analysis, such as those employing the antigen-antibody bond or ligand systems to the extent, at least in part, that the bonds occurring in vivo are detectable by means of the microsystems described, even if additional bonds are subsequently formed to reveal ex vivo or in vitro a reaction having taken place in vivo and in situ.

The apparatus of the invention offers, in particular, a significant improvement in methods of diagnosis, therapeutic indication, treatment and therapeutic follow-up, as well as in screening of drugs having originated from genomic and proteinomic (or proteomic) research.

The apparatus of the invention is noteworthy in that it is noninvasive or microinvasive and nondestructive and makes possible the remote identification of all chemical or biological substances capable of reacting more or less specifically with active substances fixed on investigation microsystems. It can involve, notably, molecules or substances present exclusively in situ in the organ or tissue or in cells (intracellular fusion). This exclusive presence is linked to the fact that these molecules or substances are rapidly metabolized outside the tissue studied as soon as they depart from their local environment. This demonstrates the importance of operating in situ with the microsystem described.

It is therefore suitable for analysis or treatment:
in vitro: on natural or genetically modified cell, tissue or organ cultures originating from specimens taken from living beings;
in vivo: under invasive or microinvasive conditions. It makes possible the guidance, orientation and positioning of the microsystem intended, notably, for molecular hybridization in situ in target cells, tissues or organs.

The apparatus of the invention is further particularly noteworthy, for it makes it possible to reach, for analysis or treatment, sites inaccessible or hard to reach by conventional methods.

The flexible rod makes it possible to bring and then position the microsystem in contact with the substrate to be analyzed, whether involving a living or expired biological material (fresh, fixed, frozen, mummified or fossilized), consisting of identical or comparable cells, mono- or multicellular tissues or organs, directly or after microeffraction of the mesothelium or protective epithelium and of the connective capsule as well as vascular endothelia in case of endovascular exploration. The flexible rod ensures the strength and cohesion of the apparatus and its flexibility and transmissibility of the movements imparted by remote control manually or robotically. The apparatus must, of course, be biocompatible and advantageously sterile, at least in its terminal part in contact with the substrate to be treated or analyzed.

The apparatus of the invention therefore includes, in addition to the microsystem where the chemical and biological reactions are carried out, a rod making possible the manual or robotic control of the apparatus.

The flexible rod controlling the apparatus makes it possible to ensure at least the following two functions:

Guidance of the microsystem up to the substrate analyzed or treated

Orientation and positioning of the microsystem in the substrate analyzed or treated, including the opening into a flexible catheter which will in turn be initially guided by an endocavitary or endovascular exploration system. In some cases the microsystem can be directly entered at the hollow end of the endocavitary or endovascular exploration system.

The flexible rod is advantageously designed to cooperate with different medical instruments used for diagnostic, therapeutic or experimental purposes. It is a question of apparatuses that are:

noninvasive, intended for the exploration of natural cavities in contact with the outside environment, like instruments for ORL, bronchopulmonary, digestive, urological or gynecological exploration;

microinvasive, with a view to exploration of natural cavities not in direct contact with the outside environment; it is then a question of instruments used in arthroscopy, colonoscopy, etc., or of endovascular exploration systems, or even superficial tissue or organ biopsy tools, notably used transcutaneously, like parenchymal effraction systems, such as needles, sharp points, cutting devices, etc.

The flexible rod is thus combined with one of those medical instruments. According to a preferred embodiment, the flexible rod is microadapted to be introduced in the above-mentioned instruments possessing an internal opening. The flexible rod can then slide into that internal opening by means possibly of a guiding groove specially provided for that purpose and thus make possible in vivo control of the apparatus of the invention in the course of different stages of a diagnostic or therapeutic exploration.

But the flexible rod can also consist of those different medical instruments themselves, which are then used as rods for control of the investigation or treatment microsystem.

The microsystem is attached to one of the ends of the flexible rod, either on the outside of the latter or inserted in the opening of said flexible rod by any means of connection. That means of connection can be a pivot system making possible the remote-controlled orientation and positioning of the microsystem in space from the flexible rod. The means of connection can consist of a deformable material electronically remote-controlled. It can also involve a biological glue, notably a type of glue used for bone tissue repair.

In all cases, the means of connection must satisfy the following criteria: adherence, strength and flexibility (resistance to handling and to stresses associated with remote-controlled movements), biocompatibility and sterility.

The apparatus of the invention can be made from a mold of adaptive configuration into which one or more homogeneous materials or electronic component materials are poured in order to take the desired shape. The means intended for making the pivot system and possibly a temporary mask can be cast at a chosen location of the mold either in the form of an intermediate device or in the form of material suitable for constructing the entire apparatus described above. It thus gains in efficiency, while retaining its functional coherence.

The means of connection can be operable by remote control to release the microsystem in situ. Thus, the apparatus of the invention comprises the two embodiments described below.

According to a first embodiment of the apparatus of the invention, the control rod makes it possible to introduce, position and then extract the microsystem after the chemical and biological reactions sought are produced in the substrate.

In order to improve contact between the microsystem placed in situ and the substrate, a rotary or back-and-forth motion can be locally imparted to the microsystem by means of the flexible guide rod, whether the latter is solid (the microsystem is then attached at its end by an appropriate system, possibly a robotic ball joint), or is hollow and tubular, in order to receive the base of the microsystem which is then partially inserted there. The objective is laceration of the tissue, or even cell lysis, through the introduction of appropriate reactive substances, conveyed by the catheter to the microsystem.

These operations are controlled either manually or by robotic assistance. For applications of analysis of a substrate, once recovered, the microsystem is analyzed in the laboratory by standard methods of revealing chemical reactions, notably of receptor/ligand type, which are produced, possibly after preparatory stages like a polymerization chain reaction. In that embodiment the microsystem is released from the flexible rod after extraction and the means of connection does not need to be remote-controlled. The means of connection must, however, ensure cohesion and sufficient flexibility to permit remote control with a view to guidance, orientation and positioning and possibly the extraction of the microsystem in situ.

According to a second embodiment of the apparatus of the invention, the means of connection between the flexible rod and the microsystem can be remote-controlled to position the apparatus on the site to be analyzed. The microsystem can be transported and positioned by means of a compatible sterile balloon. In that embodiment the microsystem can be analyzed by remote control thanks to systems of sensors making possible analysis of the chemical or biological reactions which are possibly produced in the investigation microsystem. Any microprocessor or any apparatus capable of increasing the sensitivity, efficiency and, therefore, performance of the microsystem or the remote control of placement (guidance, orientation and positioning) of the microbiochip comes within the scope and can be used within the scope of the apparatus according to the invention.

The apparatus of the invention can include a system of protection of the investigation microsystem, which is removed once the latter is brought to and positioned on the site to be analyzed. That system of protection, for example, a removable screen or deformable net, can cover the entire microsystem or only its active surface. That system of protection can be situated in the means of connection or placed in the microsystem itself.

The apparatus of the invention can include, at the end where the microsystem is attached, any system of assistance to operation of the microsystem, like a heating and/or cooling system, system for release of biological or chemical substances like buffers, development reagents, any biological alteration product or any molecules of the cell environment.

It can be supplemented by any system capable of lacerating the tissue examined or by a system introducing substances capable of planned lysis of the cells in order to have access to the content of the latter, while remaining in situ long enough for an optimal fixation reaction of the molecules of the substrate on those of the reactive layer.

The apparatus of the invention can be combined with any means making possible by remote control:
- monitoring by sensory receptors (tactile, optical, physicochemical and, notably, electronic or computer-digitized) or for any system of signal capture or processing,
- the performance of biopsies, whatever the size,
- treatment, for example, of tumors,
- local injection of chemical or biological products (cells or tissues carrying or not carrying gene vectors or components of same, as well as independent vectors), cell or tissue products, chemical or physicochemical molecular agents, and labeling agents of any kind, radioactive or not).

The apparatus of the invention can be used concomitantly or successively with means based on chemical or biological reactions other than those used in the microsystem, or with complementary means of cell laceration, cell lysis, biopsy, injection or sensory capture.

The apparatus of the invention is noteworthy in that it can be used on any type of biological or chemical substrate belonging to beings living or dead, human, animal or vegetable.

For example, it is useful in the animal, under normal conditions or under experimental conditions, for pathological studies, or in transgenic animals presenting malignant tumors or different pathological disorders, as well as in the course of cell, tissue or organ grafts in order to monitor tolerance or rejection. It makes it possible to follow the biological course of animals for the development of selective treatments, selection of animal breeds, and monitoring of viral, microbial and parasitic diseases as well as diseases from prion-type agents. The apparatus of the invention makes it possible to improve, in the animal, techniques of reproductive cloning or those intended to obtain cell lines with regenerative therapeutic activity originating from embryonal stem cells or from stem cells taken after birth called "adult" stem cells. These are cells from the vessels of the umbilical cord, but also autologous adult cells activated in vitro and presenting the characteristics of stems cells capable of being subsequently differentiated in situ, notably after guided regenerative therapy in the myocardium.

In the human being the apparatus of the invention makes it possible, noninvasively or microinvasively, to prepare the isolation and sequencing of genes and/or the identification of their functional product, to specify a diagnosis by chemical or biological methods, to identify therapeutic indications more pertinently, to test new biological preparations or new molecules with therapeutic activity, and to follow therapeutic effectiveness thanks to multistage guided examinations, repeated without major risk, considering the noninvasive or microinvasive nature of use of the apparatus. The apparatus of the invention is thus applicable to the analysis of benign or malignant tumor pathology, involving solid or fluid tumors like cancers or leukemia, and neurological, muscular, hematological, cardiovascular, metabolic or degenerative pathologies, notably whether linked or not to an identified genetic anomaly as well as to a pathological predisposition with a genetic component. The apparatus of the invention is also suitable for the practice and monitoring of cell therapy, gene therapy, regenerative treatment carried out with embryonal stem cell cultures or stem cells taken after birth or even for preimplantation diagnosis after in vitro fertilization (IVF). The apparatus of the invention is also useful in the developing human being, for example in the embryo after IVF in observance of the ethical rules in effect, in the fetus within the scope of a prenatal diagnosis with a view, notably, to the diagnosis of genetic anomalies, but also within the scope of prenatal therapy carried out in utero, in which use of the apparatus could expand the indications. The apparatus of the invention is also applicable in legal medicine and in the course of forensic investigations.

In plants or in the environmental field, the apparatus of the invention can be a valuable tool for the identification and selection of plant varieties, creation of genetically modified organisms, monitoring of viral or parasitic diseases, soil surveys and monitoring of ecological imbalances of a biological or chemical nature, thanks to in vitro and in vivo applications, notably for the identification of biological or chemical pollutants of ecosystems.

In the food and agriculture field, the apparatus of the invention is useful for the development and follow-up of GMOs, notably, for monitoring gene regulation and expression, for monitoring possible contamination throughout the food chain without prior denaturation of foodstuffs, for example for the identification of microorganisms, parasites, viruses, rickettsiae or proteins of prion type. Thus, the apparatus of the invention is useful for monitoring different stages of preservation processes, notably by freezing.

The apparatus of the invention is also of interest in the paleontological field for identification and analysis of the chemical or biological characteristics of mummified or fossilized cells, tissues and organs, with the advantage of not destroying the objects analyzed, and it makes it possible to improve the tools for identification of the different stages of the evolution of species.

The invention will be better understood by reading the following examples concerning one particular embodiment of the apparatus of the invention, in which:

BRIEF DESCRIPTION OF THE DRAWINGS

FIG. 4 represents a diagram of the support presenting a plurality of regions sensitized by an antibody, FIG. 5 shows a pilot apparatus in which the rigid plastic support is inserted in the guidance system.

This work was carried out with a system of "in situ" sampling of an analyte for its subsequent characterization in vitro. The analyte sampling was performed by immunocapture or affinity capture and the sampling system presented the following characteristics:
- rigidity,
- guidance by a flexible system,
- compound of a polymer making possible the coupling of the antibody (Ab) or of the ligand for an immunocapture or affinity capture of the analyte.

Two models were adopted for this work:

A first model entails the analysis of a disseminated candidiasis in the mouse upon disclosing antigens (Ag) of *Candida albicans* mannans type in the kidneys or liver.

A second model is based on analysis of the Engelbreth-Holm-Swarm (E.H.S.) tumor in the mouse upon disclosing laminin in the tumor of the thigh.

For study of these two models, an immunocapture system was used with the aid of anti-Candida Ab or anti-laminin Ab.

The different parameters mentioned above were studied in advance in a microplate system:
- Ab concentration for immunocapture
- Ab specificity for immunocapture
- Biotin labeling of the revealing Ab
- Detection of the biotinylated Ag by the streptavidin-enzyme complex The following characteristics of the supports were studied in an in vitro immunocapture system:
- their nature: polystyrene or other
- activation by different agents
- Ab coupling on the supports The results obtained on this work show that it is possible (i) to fix on a rigid support (joined to a flexible rod) two antibodies of different specificities (anti-Candida and anti-laminin), (ii) to sample corresponding analytes (Candida and laminin antigens), and (iii) to identify those analytes by antibodies labeled with biotin which is then revealed by a streptavidin-enzyme complex.

Figure 1:
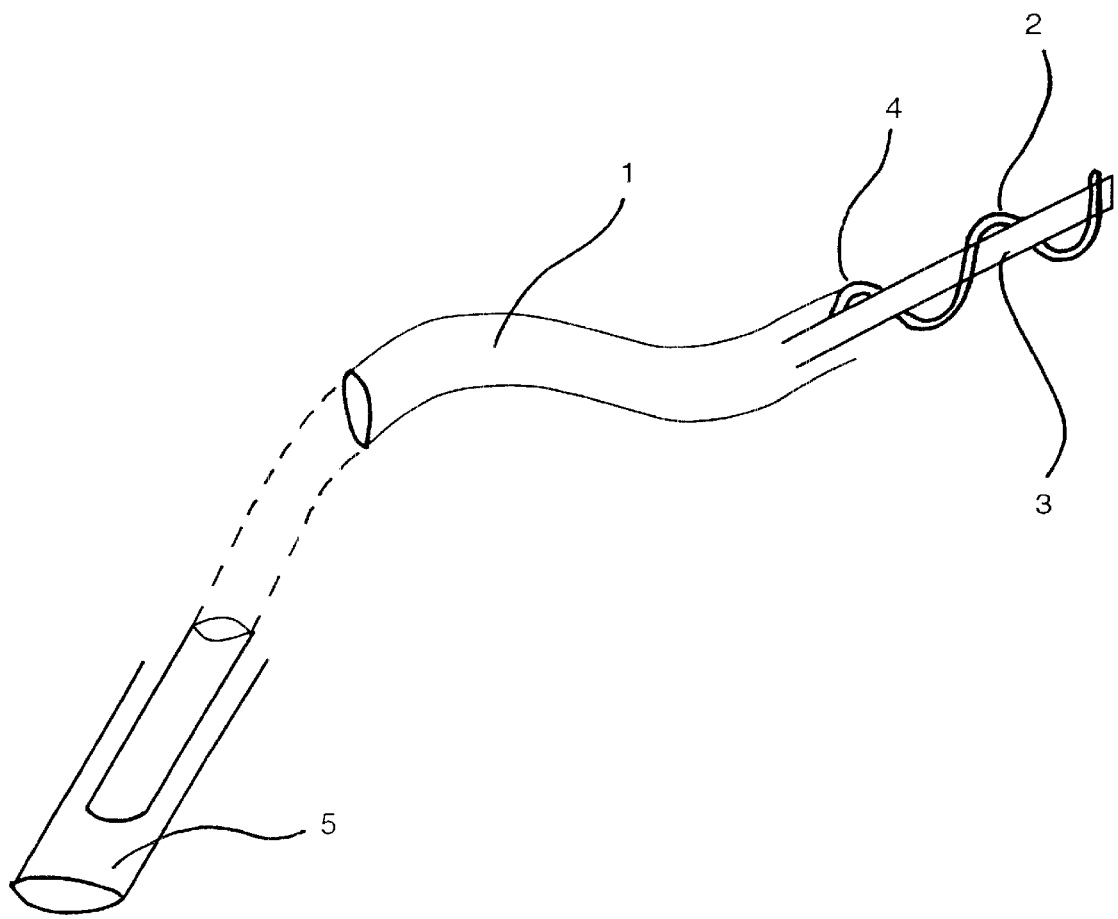
FIG. 1 represents a working example of an apparatus according to the invention.
Figure 2:
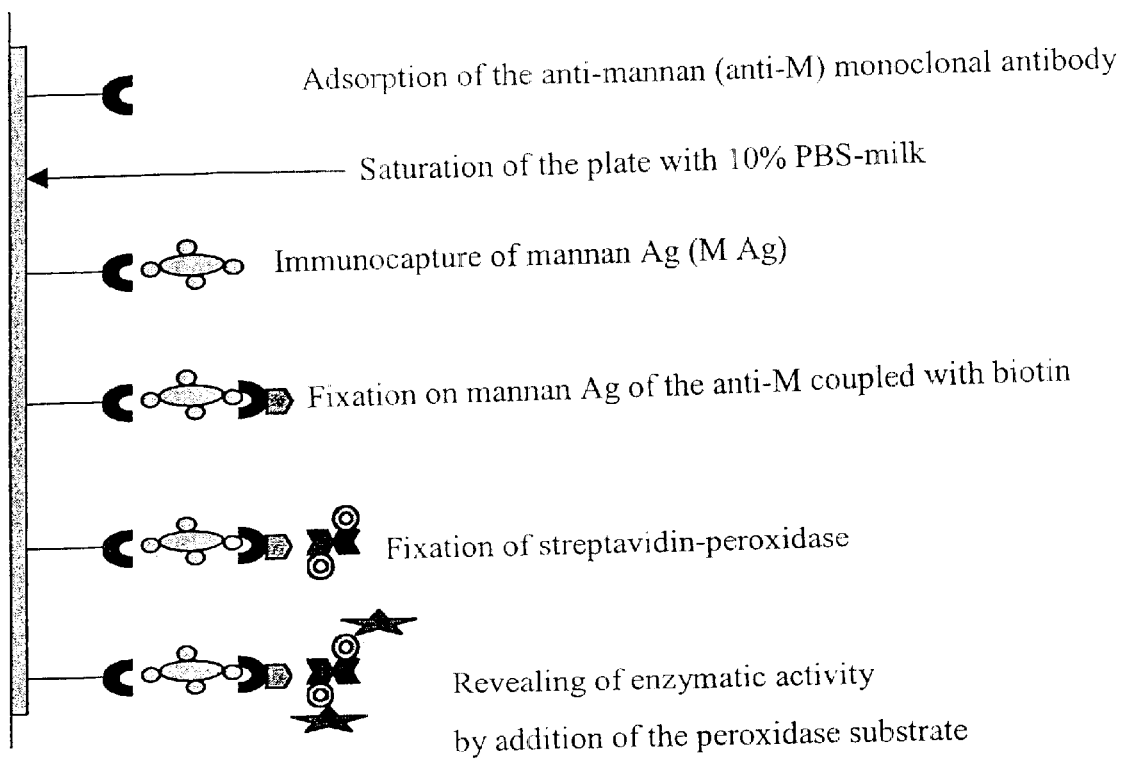
FIGS. 2 and 6 represent a general diagram of immunocapture by the ELISA method, with an anti-mannan antibody and with an anti-laminin antibody respectively.

I—Conception and Development of the System for Disclosing *C. albicans* Mannan Antigens 1) Principle of the reaction It involves an immunocapture by the ELISA method on microplate or on plastic supports (ELISA: Enzyme Linked Immuno Sorbent Assay), the principle of which is represented on the attached FIG. 2.

2) Preparation and control of the reagents a) Purification of the Anti-mannan Monoclonal Antibody (Anti-M Ab)

The anti-mannan monoclonal antibody was purified and supplied by SR2B.

b) Labeling of the Anti-M with Biotin

The purified antibody, at 3 mg/ml, is dialyzed overnight at 4° C. in the presence of borate buffer 0.1 M pH 8.8. A biotin solution (ester of 6-biotinamidocaproylamidocaproic acid and N-hydroxysuccinimide; Sigma®) at 10 mg/ml in DMSO is then added at the rate of 50 $\mu$g/mg of antibody. After 4 h of incubation at room temperature and stirring, ammonium chloride 1 M is added at the rate of 20 $\mu$l/250 $\mu$g of biotin, and the solution obtained is incubated again for 10 min. at room temperature.

After stopping of the reaction, the labeled antibody is precipitated by ammonium sulfate 2M and, after centrifugation, the base is taken up by a TBS buffer (tris-HCL 20 mM, pH 7.5, NaCl 150 mM) and dialyzed for 24 hours at +4° C. in the presence of that same buffer.

This labeled antibody is kept in aliquot form at −20° C.

c) Preparation of the Mannan Antigen

The different stages of preparation are as follows:
- Obtaining blastospores of *Candida albicans* ATCC 66396, 48 hours on Sabouraud Dextrose Agar at 22° C.
- Lyophilization of yeasts
- The lyophilisate is taken up by a citrate buffer pH 7.2, 0.2 M
- Autoclaving for 2 hours at 131° C. (1.3 bar)
- Centrifugation of the suspension for 15 minutes at 3000 rpm
- Addition of 2 volumes of absolute ethanol to the supernatant and precipitation overnight at +4° C.
- Centrifugation for 15 minutes at 3000 rpm and washing of the base with 60% ethanol;
- Centrifugation for 15 minutes at 3000 rpm and addition of acetone to dehydrate the base
- Take-up of base in distilled water The carbohydrate determination is made by the Dubois method. The carbohydrate concentration obtained is 21 mg/ml.

d) Choice of Plastic Supports

Flexible systems

Figure 3:
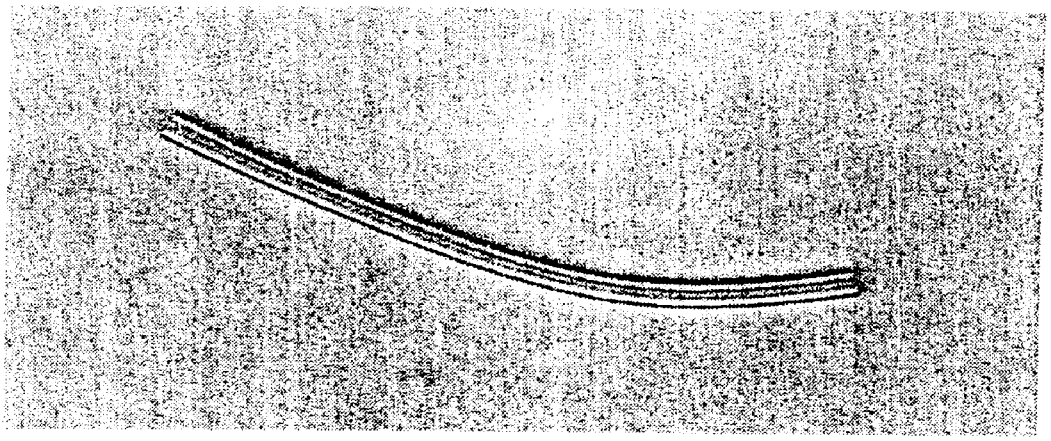
FIG. 3 shows a model of a flexible system used for guidance of the support.

Among the different flexible systems tested for guidance of the support, the one represented on the photographs given in the attached FIGS. 3 to 5 was adopted. It involves a plastic flexible hollow tube in which the support is fitted.

Rigid plastic supports

Three types of plastic supports were chosen and used for development of the system, one described as "yellow" plastic, one described as "blue" plastic and one described as "white" plastic. For each, three methods of coupling were tested, as represented on the attached FIG. 4: coupling without treatment (ø), coupling with treatment by coupling agent 1 (A1), and coupling with treatment by coupling agent 2 (A2). The three types of support were tested untreated or treated with A1 or A2 and for each system the supports were used sensitized with the anti-M Ab (U). The "white" and "blue" supports gave similar results. Only the support consisting of "white" plastic, 2 cm long and treated with coupling agent A2, was adopted for continuation of the experiments.

e) Control of Reagents and Determination of the Parameters of Sensitivity and Specificity on Microplate and on Plastic Supports in vitro On microplate The method was applied on microplate for ELISA (Greiner®). The parameters adopted for a maximum sensitivity are: concentration of the anti-M Ab for immunocapture at 1 $\mu$g/ml, saturation in 10% PBS-milk overnight at +4° C., and concentration of biotinylated anti-M Ab at 0.01 mg/ml. With those parameters the sensitivity is 0.01 $\mu$g/ml for the carbohydrate (and not mannan) concentration.

On plastic supports

The method was applied on hemolysis microtubes (Fisher®). The parameters adopted for a maximum sensitivity are: concentration of the anti-M Ab for immunocapture at 10 $\mu$g/ml, saturation in 10% PBS-milk overnight at +4° C., and concentration of biotinylated anti-M Ab at 0.02 mg/ml. With those parameters the sensitivity is 0.01 $\mu$g/ml for the carbohydrate (and not mannan) concentration.

3) Dislosure of mannan Ag ex vivo a) Determination of Parameters for Obtaining a Disseminated Candidiasis in the Mouse Use of *Candida albicans* strain ATCC 66396, culture on Sabouraud Dextrose Agar for 24 hours at 37° C.

Initial yeast concentration $10^7$/ml in NaCl 0.15M.

Inoculation of 100 $\mu$l IV in the caudal vein of the mouse.

Obtaining a disseminated candidiasis with presence of renal and hepatic abscesses.

b) Disclosure of Mannan Ag in the Liver, Kidneys and Blood

On day D=0: intravenous inoculation in mice of blastospores of *C. albicans* ATCC 66396.

On D=2, the mice are sacrificed.

The blood is collected by periorbital sampling in glass tubes and after decantation the serum is tested for mannan Ag in the bloodstream.

The kidneys or liver are sampled and placed in a sterile Petri dish. The immunocapture is carried out by placing the "white" plastic support sensitized with the anti-M Ab in those organs.

After an incubation of 15 minutes, the search for mannan Ag on the supports is made according to the principle described in vitro.

The kidneys, liver or blood of healthy mice constitute the negative controls.

c) Results

The results are expressed in optical density (OD) after subtraction of the OD of the controls, which are the healthy mice.

Concerning the kidneys, the right kidney and the left kidney of mice suffering from candidiasis were tested independently from the kidneys of healthy mice. A significant difference was observed between the signal obtained for the presence of mannan Ag in the "sick" kidneys and the signal obtained for kidneys of healthy mice (for example, the optical density difference is approximately 0.4).

Concerning the liver, the mannan Ag were also detected by the probe with a significant difference (optical density difference 0.6).

In the blood (diluted to 1/10) of healthy mice or mice suffering from candidiasis, no mannan Ag were detected in the bloodstream.

II—Conception and Development of the System for Disclosure of Laminin

1) Principle of the reaction

Figure 6:
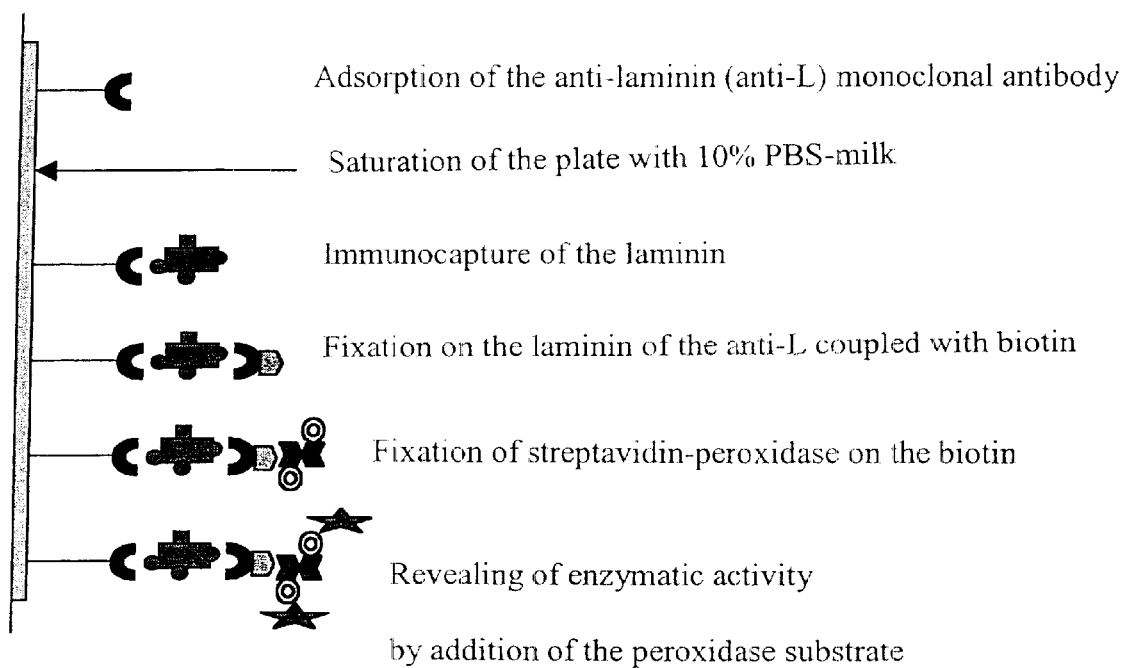

It involves an immunocapture by ELISA method on microplate or on plastic supports (ELISA: Enzyme Linked Immuno Sorbent Assay), the principle of which is represented on the attached FIG. 6.

2) Preparation and control of reagents a) Labeling of the Anti-laminin Antibody (Anti-L Ab) with Biotin The antibody adopted for developing the detection of laminin is a polyclonal antibody produced in the rabbit and purified by affinity (Rockland®). The method of labeling with biotin is identical to that used for the anti-M.

b) Laminin

The laminin adopted for in vitro development is the purified laminin from mice (Sigma®).

c) Choice of Plastic Supports

Flexible systems, as previously described for *Candida albicans*.

Rigid plastic supports, as previously described for *Candida albicans*.

d) Control of Reagents and Determination of the Parameters of Sensitivity and Specificity on Microplate and on Plastic Supports in vitro On Microplate The method was applied on microplate for ELISA (Greiner®). The parameters adopted for a maximum sensitivity are:

Concentration of the anti-L Ab for immunocapture at 5 µg/ml.

Saturation in 10% PBS-milk overnight at +4° C.

Concentration of biotinylated anti-M Ab at 5 µg/ml.

With those parameters, the sensitivity is 0.01 mg/ml for the laminin concentration.

On Plastic Supports

The method was applied on hemolysis microtubes (Fisher®). The parameters adopted for a maximum sensitivity are the same as on microplate, namely:

Concentration of the anti-L Ab for immunocapture at 5 µg/ml.

Saturation in 10% PBS-milk overnight at +4° C.

Concentration of biotinylated anti-L Ab at 5 µg/ml.

With those parameters, the sensitivity is 0.01 mg/ml for the laminin concentration.

4) Disclosure of laminin ex vivo a) Determination of Parameters for Obtaining a "Laminin" Tumor Visible to the Naked Eye Thawing of the E.H.S. (Engelbreth-Holm-Swarm) sarcoma in the mouse.

Inoculation in the thighs of mice.

After three weeks the mice are sacrificed, and tumor samples are taken, ground up and inoculated in other mice.

b) Disclosure of Laminin in the Tumor of the Thigh in the Mouse

The mice are sacrificed and immunocapture is carried out by placing the "white" plastic support sensitized with anti-L in the tumor of the thigh. Thighs of healthy mice constitute the negative controls.

c) Results

The results are expressed in optical density (OD) after subtraction of the OD of the controls, which are the healthy mice.

A significant difference is observed between the signal obtained for the presence of laminin in the tumor and the signal obtained for thighs of healthy mice (for example, the optical density difference is approximately 0.3).

III—Coupling of the Two Systems: Simultaneous Detection of Mannan Ag and Laminin ex vivo 1) Sensitization of the probe The support constituted by the "white" plastic and maintained by the flexible guidance system is sensitized with the anti-M Ab and anti-L Ab at the previously established concentrations.

2) Disclosure of mannan Ag and laminin ex vivo

The immunocapture is carried out in:

healthy mice (controls)

mice suffering from candidiasis mice with a laminin tumor (E.H.S.).

Supports are:

placed first in the kidneys or liver of a mouse suffering from disseminated candidiasis and then in the tumor (E.H.S.) of the thigh of another mouse, or placed first in the tumor (E.H.S.) of the thigh of one mouse and then in the kidneys or liver of another mouse suffering from disseminated candidiasis.

The supports are then revealed by the anti-M or anti-L or a mixture of both.

Negative controls are made by placing supports in the kidneys or liver of a healthy mouse and then in the thigh of the same mouse (and vice versa).

3) Results

The results are expressed in optical density (OD) after subtraction of the OD of the controls, which are the healthy mice.

Whatever the order in which the support is implanted in the different organs, the mannan Ag or the laminin is significantly detected in relation to the healthy mice, when the system is revealed by only one of the two antibodies (OD: 0.4 for the mannan Ag and 0.4 for the laminin).

When the mixture of both biotinylated antibodies is used for revealing, the signal obtained is much higher (for example, mouse with candidiasis+laminin OD=0.7).

The mannan Ag could not be detected in the blood of the healthy mice or of the mice suffering from disseminated candidiasis.

What is claimed is:

1. An apparatus comprising a support which is capable of non-fluorescent biological assaying or active agent delivery; a flexible rod; a system for protecting the support, and a system capable of lacerating a tissue,
wherein one end of the flexible rod is attached to the support and the other end of the flexible rod is attached to a device, which controls the movement of said support, and
wherein the flexible rod is encased in an internal opening of a diagnostic, therapeutic or experimental medical instrument.

2. The apparatus of claim 1, wherein the support is capable of non-fluorescent biological assaying.

3. The apparatus of claim 2, wherein the support comprises an array of chemical or biological substances.

4. The apparatus of claim 3, wherein the support comprises an array of at least 2 chemical or biological substances.

5. The apparatus of claim 3, wherein the support comprises an array of at least 100 chemical or biological substances.

6. The apparatus of claim 3, wherein the support comprises an array of at least 1000 chemical or biological substances.

7. The apparatus of claim 3, wherein the chemical or biological substances are capable of reacting with one or more target substances present in a substrate.

8. The apparatus of claim 3, wherein the chemical or biological substances are one or more substances selected from the group consisting of a receptor, a ligand, an antigen, an antibody, a peptide, a polypeptide, a protein, and a polynucleotide.

9. The apparatus of claim 8, wherein the chemical or biological substances are polynucleotides.

10. The apparatus of claim 8, wherein the chemical or biological substances are one or more of a peptide, a polypeptide or a protein.

11. The apparatus of claim 1, wherein the end of the flexible rod attached to the support further comprises at least one pivot attached to the support.

12. The apparatus of claim 1, wherein the support is in the form of a ribbon and is wound around the end of the flexible rod.

13. The apparatus of claim 1, which further comprises a heater or cooler positioned at the end of the substrate.

14. The apparatus of claim 1, wherein the support is capable of active agent delivery.

15. The apparatus of claim 14, wherein the active agent is a pharmaceutically active agent.

16. The apparatus of claim 14, wherein the active agent is at least one agent selected from the group consisting of a nucleic acid, a protein, and an antibody.

17. The apparatus of claim 1, which further comprises a biopsy device.

18. The apparatus of claim 1, wherein the system of protecting the support is the internal opening of the diagnostic, therapeutic, or experimental medical instrument.

19. The apparatus of claim 1, wherein the flexible rod is capable of sliding in the internal opening of the diagnostic, therapeutic, or experimental medical instrument.

20. A method of assaying a biological sample, comprising contacting the biological sample with the support of the apparatus of claim 3 to assay the biological sample.

21. The method of claim 20, wherein the biological or chemical substances are one or more substances selected from the group consisting of a receptor, a ligand, an antigen, an antibody, a peptide, a polypeptide, a protein, and a polynucleotide.

22. The method of claim 21, wherein the chemical or biological substances are polynucleotides.

23. The method of claim 21, wherein the chemical or biological substances are one or more of a peptide, a polypeptide or a protein.

24. The method of claim 20, wherein the support comprises an array of at least 2 chemical or biological substances.

25. The method of claim 20, wherein the support comprises an array of at least 100 chemical or biological substances.

26. The method of claim 20, wherein the support comprises an array of at least 1000 chemical or biological substances.

27. The method of claim 20, wherein the biological sample is a natural cell, genetically modified cell, tissue culture, or organ culture.

28. The method of claim 20, wherein the biological sample is an in vivo cell, tissue, or organ.

29. A method of delivering an active agent to a location in a patient, comprising inserting the apparatus of claim 14 to the location in the patient, and delivering the active agent.

30. The method of claim 29, wherein the active agent is a pharmaceutically active agent.

31. The method of claim 29, wherein the active agent is at least one agent selected from the group consisting of a nucleic acid, a protein, and an antibody.

* * * * *